United States Patent [19]

Gibbard

[11] 3,994,591

[45] Nov. 30, 1976

[54] METHOD AND APPARATUS FOR SELECTING BETWEEN DIFFERENTLY COLORED FEATURES

[75] Inventor: David William Gibbard, Royston, England

[73] Assignee: Cambridge Analysing Instruments Limited, England

[22] Filed: Jan. 29, 1975

[21] Appl. No.: 545,025

[30] Foreign Application Priority Data
Jan. 31, 1974 United Kingdom.............. 4468/74

[52] U.S. Cl................................ 356/178; 356/39; 356/186
[51] Int. Cl.²............................................. G01J 3/48
[58] Field of Search............ 356/39, 178, 189, 186; 178/7.2, 7.6, 7.7

[56] References Cited
UNITED STATES PATENTS
3,851,156  11/1974  Green.............................. 356/39 X Primary Examiner—John K. Corbin
Assistant Examiner—F. L. Evans
Attorney, Agent, or Firm—Oblon, Fisher, Spivak, McClelland & Maier

[57] ABSTRACT

A method and apparatus for analyzing features in a field which is scanned to produce video signals according to the spectral characteristics of the features. The apparatus incorporates two or more filters for producing different spectral characteristic images of the field which are then synchronously scanned using a plurality of separate scanners which are synchronized but which need not be so accurately registered point by point as is normally the case with color scanners. The invention provides for the use of an anti-coincidence detector circuit to associate video signal information arising from scanning non-registered images of the features in the field so that the information in the separate channels can be associated and made available for simultaneous comparison so that a ratio can for example be obtained of the integrated optical density measurements of a feature in respect of different color components of the image of the feature.

Another embodiment of the invention is described in which an additional parameter such as area can be measured and a feature classification performed taking both integrated optical density ratios and areas into account.

A third embodiment of the invention is described in which additional threshhold comparators are incorporated so that different areas of detected features can be selected for measurement.

13 Claims, 6 Drawing Figures

METHOD AND APPARATUS FOR SELECTING BETWEEN DIFFERENTLY COLORED FEATURES

This invention concerns a method and apparatus for analysing an image of a field containing features of differing spectral characteristic (such as colour) or regions of features so as to produce electrical signals relating to parameters of features or regions thereof, which have a common characteristic with regard to colour.

The invention is of particular application in the analysis of blood cells which have been stained with red and blue dyes. Different parts of different cells take up the dyes in differing quantities so that the resulting colours of cells in a specimen of the blood can range from blue through purple to red.

By operating two scanners synchronously and forming two images of the same field onto the two scanners, the two images being obtained by using two different light filters, two video signals can be obtained, the one corresponding to the features in the field having a first colour characteristic as determined by the one filter and the other to features having a second colour characteristic as determined by the other filter.

However, considerable difficulty is experienced in operating two or more scanners synchronously and in exact registration so that the position of the scanning spot in each scanner is exactly the same so that for the other scanner at each instant during the scanning of the field. If the registration between the various scanners is not exact, amplitude excursions in the resulting video signals which purport to relate to the same feature in the field, will occur at slightly different points in time. In consequence it is not possible to guarantee that where the amplitude excursions (or signals derived therefrom) in each video signal are combined to generate an electrical signal whose value is proportional to a parameter of the feature, that this electrical signal will be released at the same instant in time during the scanning of the two separate images supplied to the two different scanners. If they do not occur simultaneously it is possible to combine the two electrical signals for each picture so as to provide differential information relating to the colour of the scanned feature.

On the other hand it is possible to arrange that the registration is sufficiently accurate so that there will always be some overlap between the amplitude excursions in two video signals obtained from two synchronised scanners set to scan two images obtained from the same field, using different light filters.

It is an object of the present invention to provide a method of analysing a field of features of different spectral characteristic (such as colour) using two or more separate scanners and different optical filters to generate a corresponding number of video signals each corresponding to features or regions thereof having a particular spectral characteristic.

According to the present invention a method of analysing features in a field according to their spectral characteristics comprises the steps of illuminating the field, filtering the light according to its wavelength from the illuminated field to produce a plurality of separate images of the field, synchronously scanning each of the plurality of separate images to produce a corresponding plurality of video signals the amplitudes of which vary in accordance with variations in illumination intensity within the particular image which is presented to that scanner, comparing each separate video signal with a reference voltage and generating a train of constant amplitude pulses in place of each video signal a pulse being generated whenever the amplitude of the video signal bears a given relationship to the reference voltage with which it is compared, and computing from a signal derived from the video signal an electrical signal whose value corresponds to a parameter of at least part of each feature and storing each said computed signal, combining the plurality of trains of constant amplitude pulses by means of a circuit device having an OR- function to produce a pulse train corresponding to that which would be obtained from scanning an image formed by superimposing the said plurality of different images, delaying the composite image pulse train for approximately one line scan period, comparing the pulses in the delayed composite image signal with the pulses in the current composite image signal, generating an anti-coincidence pulse at the end of a delayed composite image signal pulse for which there is no corresponding pulse in the current composite image signal and releasing the stored computed signals associated with a composite image in response to the generation of the anti-coincidence pulse therefor.

The signal derived from the video signal may be a signal comprising the logarithm of the analogue video signal amplitude values or a signal comprising constant amplitude pulses produced by comparing the video signal with a reference voltage.

The values of the stored computed signals for each feature may be compared on release by forming a ratio.

An anti-coincidence detector for generating an anti-coincidence pulse in this manner from constant amplitude pulses supplied thereto is described in British Pat. Specification No. 1,264,804 and U.S. Pat. No. 3,619,494.

The effect of the invention is to generate for each feature an electrical window which will be somewhat larger in area than the original feature (the exact enlargement being determined by the degree of mis-registration between the synchronised scanners). As described in the aforementioned British and U.S. Pat. a signal corresponding in value to a parameter of a feature (such as area or integrated density) can be computed in a specially designed computing circuit (described as an associated parameter computer) and the electrical parameter signal associated in time and position during the scanning with the relative position of the feature in the scanned field. The operation of the associated parameter computer is at least in part controlled by signals from an anti-coincidence detector also described therein and the parameter signal for a feature is released from the computer by the anti-coincidence pulse for that feature.

According to a preferred feature of the present invention each of the plurality of constant amplitude pulse trains or each of the plurality of video signals obtained from scanning the different images is supplied as the input signal to an associated parameter computer of the type previously described and the plurality of computers are controlled by a single anti-coincidence detector of the type previously described and which is itself supplied with the constant amplitude pulses corresponding to the composite image.

British Pat. Specification No. 1,323,556 and U.S. Pat. No. 3,624,604 describe the method of operating a plurality of separate parameter computers synchronously from a single anti-coincidence detector circuit.

Preferably a first associated parameter computer for each scanner generates an electrical signal whose value is proportional to the area of the image of each feature seen by that scanner and for which the amplitude excursions in the video signal are detected.

Preferably a second associated parameter computer is provided for each scanner to which is supplied for each detected amplitude excursion a signal whose value is proportional to the integral of the logarithm of the video signal amplitude values occurring during that detected amplitude excursion.

The invention will now be described by way of example with reference to the accompanying drawings in which.

Figure 1:
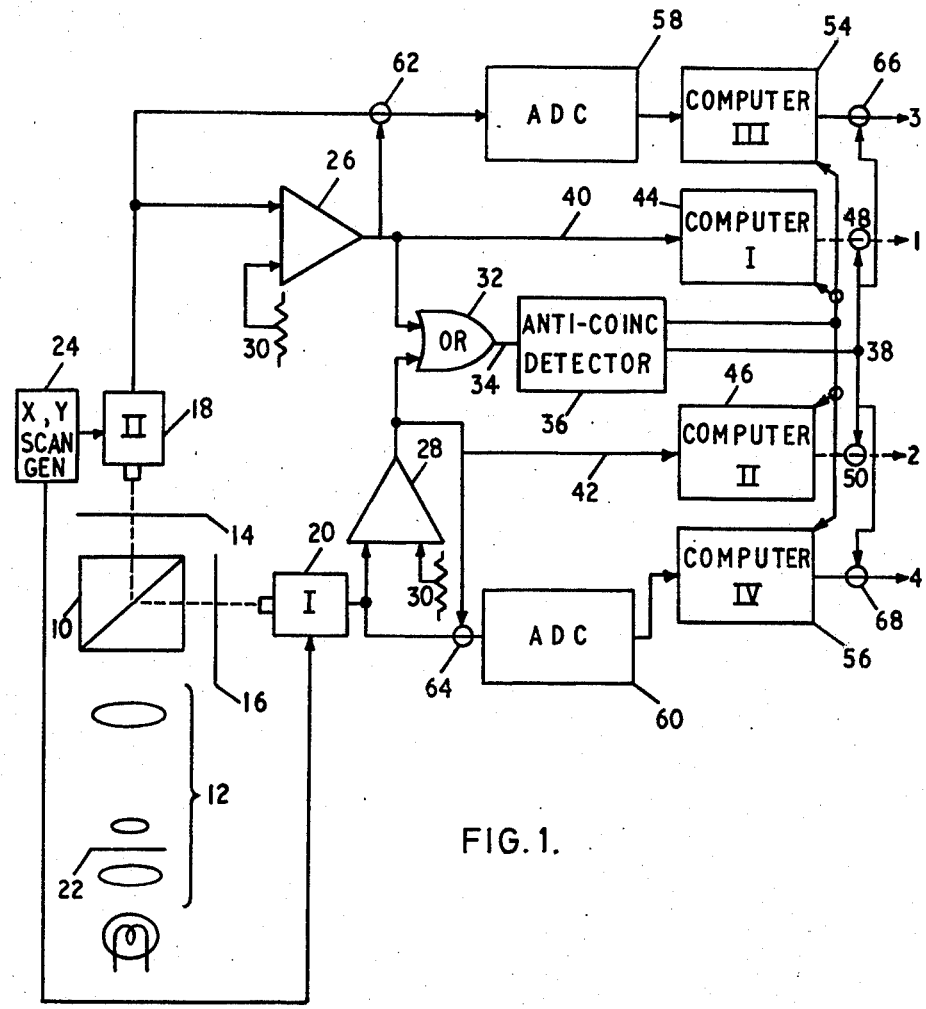
FIG. 1 is a block circuit diagram of part of an image analysing computer constructed in accordance with the invention.

As shown in FIG. 1 a beam splitting prism 10 diverts the real image obtained from a microscope optical system 12 through two optical filters 14 and 16 which pass certain different wavelengths of light to the two scanners 18 and 20. Two final images are formed on the scanned targets of two scanners 18 and 20 respectively. The two scanners conveniently comprise two similar high resolution television cameras.

The image may for example be that of a blood smear contained on a microscope slide 22, the blood cells having first been stained using red and blue dyes in known manner.

The deflection signals for the two scanners 18 and 20 are derived from a single scan deflection signal generator 24 and although not shown, synchronising circuits are provided for ensuring that the two scanners operate in synchronism and that a reasonable level of registration is obtained between the positions of the two scanning spots.

The video signal output from each scanner constitutes one input to each of two amplitude comparators 26 and 28. The other input is supplied with a reference voltage which may be derived for example from a potentiometer denoted in each case by the reference numeral 30. Alternatively the reference voltage may be derived automatically so that its value bears some relationship to the light output and/or the peak to peak values of the video signal amplitude excursions. Each comparator produces a two value output signal, one value of which exists whilst the video signal amplitude is lower than the reference voltage and the other value of which exists when the video signal amplitude exceeds the reference voltage value. Each video signal is therefore converted into a series of constant amplitude pulses the durations of which correspond to the durations of the amplitude excursions of the original video signal which exceed (or are below) the reference voltage.

The two trains of constant amplitude pulses which can therefore be considered as binary signals are applied to an OR-gate 32 so that the output signal along line 34 is a composite signal which corresponds to the logical combination of the two input signals to the OR-gate.

If the output signal on line 34 were displayed on a monitor screen, the latter would present a picture containing contrasting areas approximately centered on the positions of the actual features in the original field at 22 but enlarged and slightly misshapen due to registration inaccuracies between the two scanners 18 and 20.

The composite signal along line 34 is applied as one input to an anti-coincidence detector circuit 36. This circuit includes a delay device for delaying the signals along line 34 by approximately one line scan period and a comparator for comparing the output of the delay device (not shown) with the signal currently applied along line 34. The detector circuit 36 generates an output signal pulse along line 38 at the end of a delayed constant amplitude pulse for which there is no corresponding pulse at the input of the detector 36. This output pulse is known as an anti-coincidence pulse and only one such pulse is generated for each composite feature area as seen by the detector and formed by the non-registration of the feature signals from the scanners.

Additionally the constant amplitude pulses from the two detectors are supplied along lines 40 and 42 as input signals to two associated parameter computers 44 and 46 respectively. Each computer is adapted to generate an electrical signal whose value corresponds to the area of the feature whose amplitude excursions are detected by the detector 26. The operation of the computer is to add an increment of area information to form an accumulating total of area information for each detected feature, the accumulating total being held in a recirculating memory. An increment of area information for a feature arises during each line scan intersection with that feature and the electrical signal corresponding to the total accumulated value of all the area increments is released when the anti-coincidence pulse for that feature is supplied along line 38 to the computer. The anti-coincidence pulses for the various composite features which appear along line 38 are shown as controlling the operation of gates in the outputs of the computers 44 and 46, the two gates being labelled 48 and 50 respectively. In this way, since a single pulse is used to control the two gates, the two values computed by the two computers 44 and 46 are released simultaneously.

Although simple, gates 48 and 50 have been shown, in practice these would be suitable addressing devices for causing the content of the recirculating memory to be released at that point in the scan.

Additional connections are shown between the anti-coincidence detector circuit 36 and the computers 44 and 46. These signal paths convey updating control signals to the two computers at the end of each composite signal constant amplitude pulse sometime after the end of each constant amplitude composite signal pulse which appears at the input of the detector 36. These signals are used to update the recirculating information in each computer memory.

Figure 3:
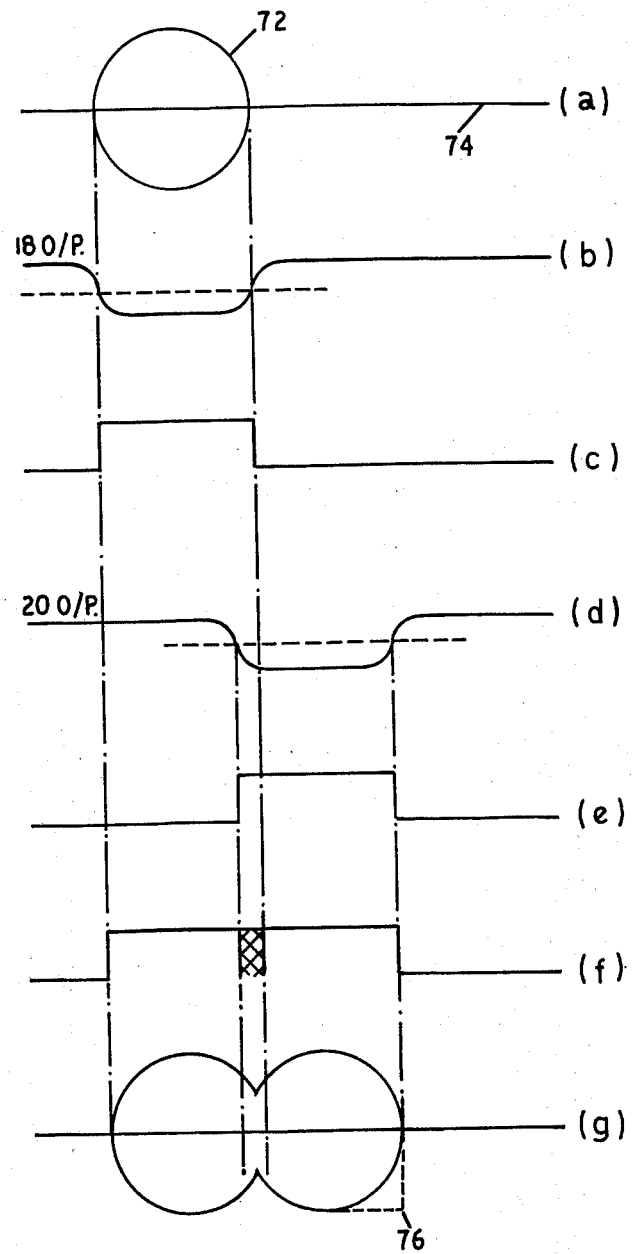
FIG. 3 is a set of wave forms illustrating the way in which electrical signals arising from synchronous scanning of different images of the same field are associated using the method according to the present invention.

FIG. 3 illustrates a cell 72 which is intersected by a scanning line 74. The video signal obtained from scanner 26 is shown at FIG. 3*b* and the video signal from scanner 28 is shown at FIG. 3*d*. The constant amplitude pulse derived from the amplitude excursion corresponding to the line scan intersection of feature 72 for scanner 26 is shown at FIG. 3*c* and likewise for scanner 28 at FIG. 3*e*.

The operation of the OR-gate 32 is shown in FIG. 3*f* in which the two constant amplitude pulses combine to produce a composite constant amplitude pulse of duration determined by the duration of the two individual pulses and the degree of overlap thereof.

If all the constant amplitude pulses derived in this way for a feature 72 are then displayed on a monitor screen the result is shown at FIG. 3*g* and the position of the anti-coincidence pulse for this composite feature is denoted by reference number 76. This is the position in the scan at which the anti-coincidence pulse for the composite feature is released by the anti-coincidence detector 36.

Application I

The apparatus shown in FIG. 1 may be used to analyse a field of non-nucleated blood cells which have been stained by red and blue dyes. In such an application where the object is to distinguish between cells which have predominantly taken up red stain and other polychromitic cells which also take up substantial quantities of blue stain, the two filters 14 and 16 are arranged to filter out respectively blue and red wavelengths so that the video signal from the scanner 18 will only relate to red stained cell content and the video signal from scanner 20 will only relate to blue stained cell content.

Comparators 26 and 28 are supplied with reference voltages from potentiometers 30 and the values of the reference voltages are selected so that constant amplitude pulses are generated whenever a cell of either type is scanned by either scanner.

The analogue amplitude values of the video signal released by gate 62 undergo a logarithmic conversion and are then digitised by an analogue to digital convertor 58 and are accumulated by an AP computer 54. Likewise the analogue amplitude values of the video signal released by gate 64 also undergo a similar logarithmic conversion and are then digitised by analogue to digital convertor 60 and are accumulated by an AP computer 56. The values in the two computers 54 and 56 for each cell correspond to the red and blue components of the integrated optical density of the cell.

Figure 2:
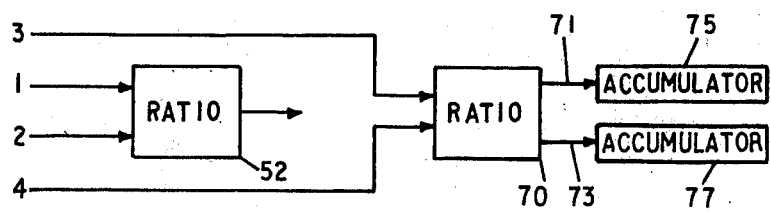
FIG. 2 is a block circuit diagram illustrating how the signals obtained from the computer of FIG. 1 may be employed.

As previously described the end of scanning of a particular cell is detected by the anti-coincidence detector 36 and the two integrated density component values are released by operation of gates 66 and 68 by the output from detector 36. The two values so released may be compared in a ratio circuit such as 70 shown in FIG. 2, the numerical value of the ratio being a measure of the "colour" of the cell.

The blue to red ratio is equal to the ratio of signal 4 to signal 3 from the computers 54 and 56 and will be above a critical value (which can in practise be determined by experiment) if the cell is polychromatic. The ratio circuit 70 is arranged to produce a count pulse on line 71 if the ratio is above the critical value and a count pulse on line 73 if the ratio is below the critical value. The two accumulators 75 and 77 serve to count separately the numbers of such count pulses so released to give at the end of a frame scan the total number of polychromatic cells (in 75) and the total number of other cells (in 77) for the field just scanned. By continually accumulating such information from successive scans of different fields of view of the specimen a total count relating to the different types of cell present in a specimen can be obtained.

Application II

In a modification of Application I, the object is to classify cells according to their size as well as their colour. To this end pulses from 26 and 28 are supplied via lines 40 and 42 to two AP computers 44 and 46 each adapted to compute the area of cells from the constant amplitude pulses relating thereto. The area value for each cell is released from computer 44 by gate 48 and computer 46 by gate 50. The two values should be substantially the same but if a cell is undetected in one of the channels (for example from scanner 20) it is important that the higher value is selected. To this end a comparator 52 is provided for releasing whichever is the higher of the two area values.

The area value released can be employed in conjunction with the signals from the ratio circuit 70 to obtain, for example, a size distribution for both classes of cells or simply to eliminate count pulses for cells of either or both type outside a given area size range.

Application III

Applications I and II described above relate to non-nucleated cells only. Where nuclei are present other distinguishing features may be employed for selecting between cells. In practice selection between cells is normally undertaken using a number of different parameter measurements and the final classification made only after the results of the various parameter measurements have been considered. The following application of the present invention illustrates one such parameter measurement, i.e. the selection between cells on the basis of differently coloured nuclei.

Figure 4:
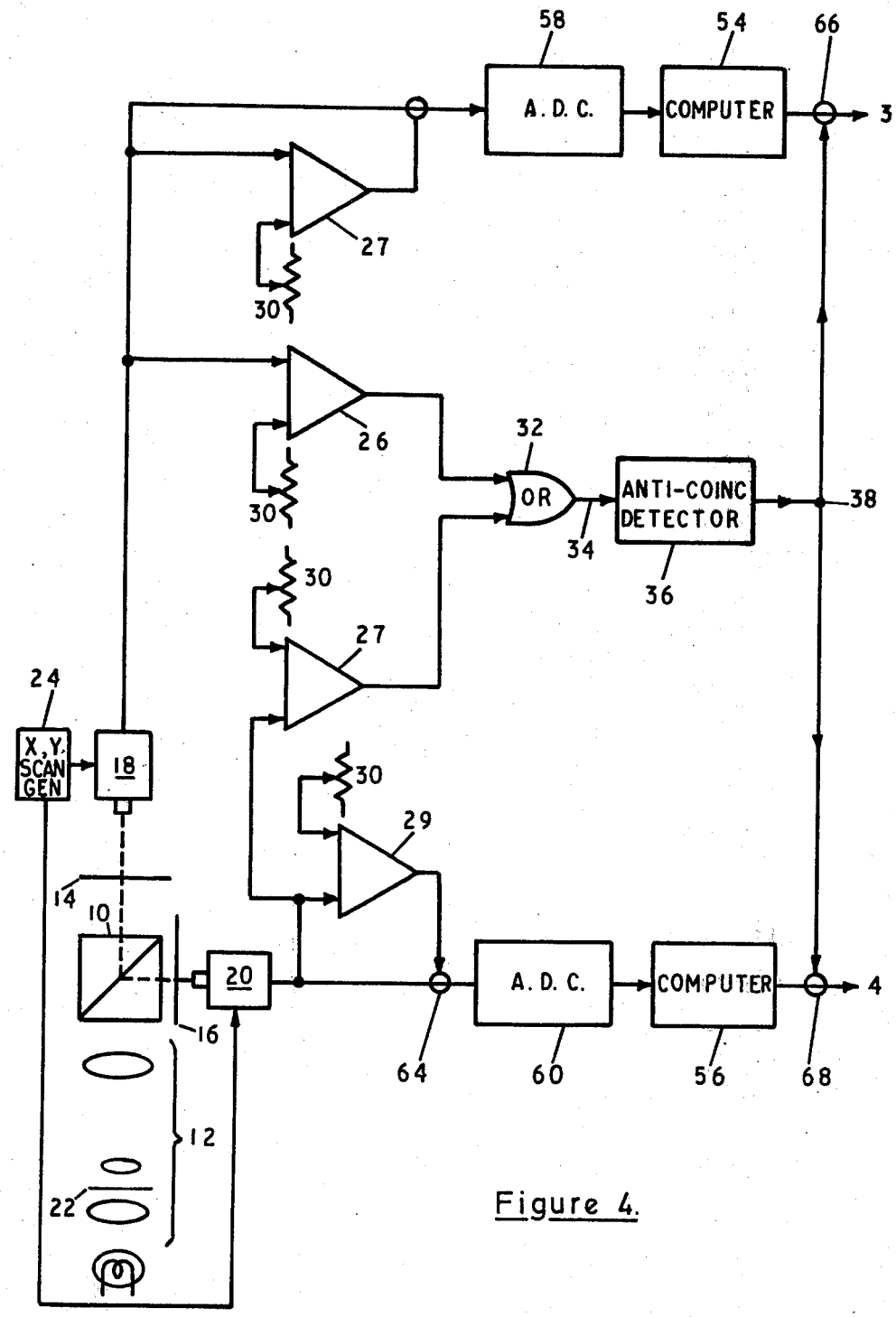
FIG. 4 is a block circuit diagram similar to FIG. 2 which includes additional comparators.
Figure 5:
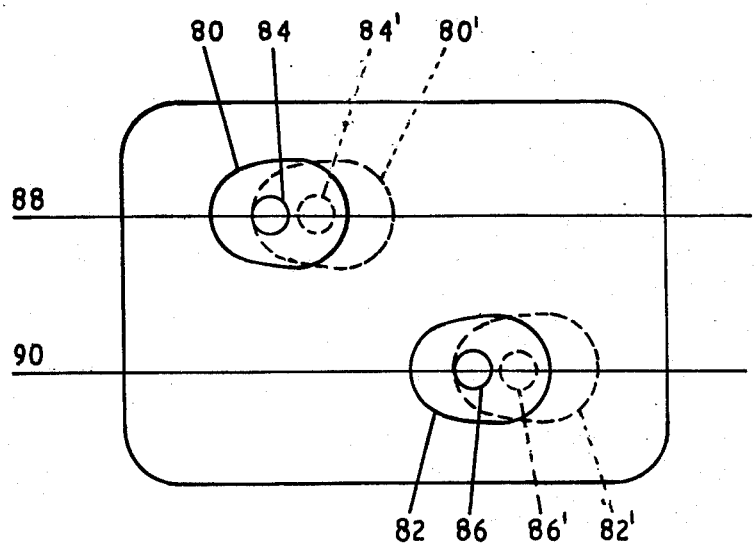
FIG. 5 illustrates a field containing two nucleated cells.
Figure 6:
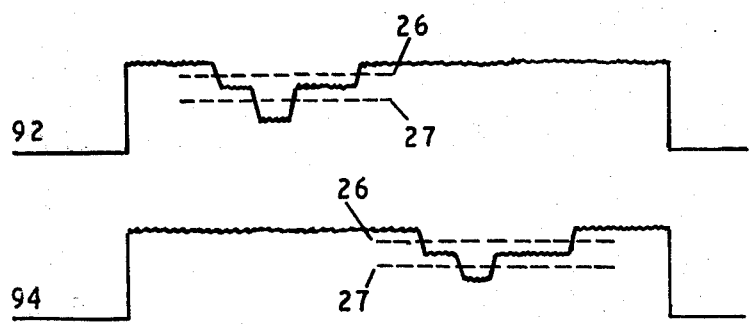
FIG. 6 illustrates diagrammatically the video signal obtained on two typical scan lines intersecting the two cells.

The FIGS. 4, 5 and 6 of the drawings relate to this third Application of the invention. Dealing first with FIG. 5, there is shown a field of view containing two cells 80 and 82 each of which comprises a tinted cytoplasm and a darker and differently coloured nucleus 84 in the case of cell 80 and 86 in the case of cell 82. It is assumed for the purposes of this description that the nucleus 84 is a deep purple while the nucleus 86 is a blue colour.

Shown dotted are the misregistered images of the cells and nuclei due to inaccurate registration between the scanners and it is assumed that although the registration does not necessarily allow overlap between the nucleus in the one image and that in the other of one cell, the two images of the one cell such as 80 and 80′ will always overlap.

Two typical scan lines are denoted by lines 88 and 90 in FIG. 5. The video signals which arise during the scanning of lines 88 and 90 in one of the scanners only are denoted on lines 92 and 94 in FIG. 6 and the reference voltages applied to the two comparators 26 and 27 which apply to that channel (from scanner 18) in FIG. 4 are denoted by correspondingly numbered lines 26 and 27 in FIG. 6.

The substantial difference obtained between the amplitude excursion for the nucleus 84 and that of nucleus 86 is obtained by using an appropriate filter 14 which cuts out all blue wavelength light from scanner 18.

It will be appreciated that the relative amplitudes of the nucleus signals from scanner 20 can be made to be the reverse of those shown in FIG. 6 for scanner 18 by incorporating a suitable filter 16 which cuts out red wavelength light from the scanner 20.

The circuit FIG. 4 is similar to that of FIG. 1 except that computers 42 and 44 have been left out and two additional comparators 27 and 29 have been included. Comparator 27 is supplied with the video signal from scanner 18 and a reference voltage set by potentiometer 30 and serve to control gate 62 instead of the output from comparator 26 which is simply supplied to the OR-gate 32. Likewise the additional comparator 29 serves to control the operation of gate 64 instead of the output signal from comparator 28 which, like the output from 26 is simply supplied straight to the OR-gate 32.

The OR-gate 32 functions exactly as before and the area seen by the anti-coincidence detector 36 corresponds to the total area of the two partially superimposed cell images such as 80 and 80'. Any feature information arising during the scanning of that total area is thus associated by the anti-coincidence detector and this allows information arising from two non-overlapping nuclei images to be associated.

Whilst the OR-gate 32 is receptive of constant amplitude pulses from comparators 26 and 28 which define the large area of the partially superimposed cytoplasm images, the gates 62 and 64 only open while the comparison criterion set by comparators 27 and 29 is satisfied. The potentiometers 30 serving these two comparators are set so that the reference voltages supplied thereto exceed the amplitude excursions of the video signal corresponding to the cytoplasm cells but are intersected by the amplitude excursions of the video signal relating to the nuclei. Consequently the gates 62 and 64 are only opened whilst the nuclei are being scanned and the integrated density information accumulated in computers 54 and 56 only relates to the information arising from the scanning of the nuclei. Consequently the values in computers 54 and 56 will be the red and blue components of the integrated optical density of the nuclei and these values can be released at the end of scanning the appropriate cell images on the appearances of the output signal from the anti-coincidence detector 36.

The signals released by gates 66 and 68 may be supplied as previously to a ratio circuit 70 but the numerical values accumulated in the accumulators 75 and 77 will relate to the numbers of cells classified as having nuclei of one colour or another rather than on the basis of the overall colour of the cells as is the case with non-nucleated cells in the example described in Application I.

I claim:

1. A method of analysing features in a field according to their spectral characteristics comprising the steps of illuminating the field, filtering the light according to its wavelength from the illuminated field to produce a plurality of separate images of the field, synchronously scanning each of the plurality of separate images to produce a corresponding plurality of video signals the amplitudes of which vary in accordance with variations in illumination intensity within the particular image which is presented to that scanner, comparing each separate video signal with a reference voltage and generating a train of constant amplitude pulses in place of each video signal whenever the amplitude of the video signal bears a given relationship to the reference voltage with which it is compared, computing from a signal derived from the video signals separate electrical signals whose value correspond to a parameter of at least a part of each feature and storing each said computed signal, combining the plurality of trains of constant amplitude pulses by means of a circuit device having an OR- function to produce a pulse train corresponding to that which would obtained from scanning an image formed by superimposing the said plurality of different images, delaying the composite image pulse train for approximately one line scan period, comparing the pulses in the delayed composite image signal with the pulses in the current composite image signal, generating an anti-coincidence pulse at the end of a delayed composite image signal pulse for which there is no corresponding pulse in the current composite image signal and releasing the stored computed signals associated with a composite image in response to the generation of the anti-coincidence pulse therefor.

2. A method as claimed in claim 1 further comprising the step of forming a ratio of the values of the stored computed signals released for each feature and generating a signal indicating the value of the ratio.

3. A method of analysing features in a field according to their spectral characteristics as claimed in claim 1 wherein the signal derived from the video signal is a signal comprising the logarithm of the analogue video signal amplitude values which are accumulated to form the said stored computed signal for the feature, the parameter computed for the feature or part thereof therefore comprising the integrated optical density thereof.

4. A method as claimed in claim 3 further comprising the step of forming a ratio of the values of the stored signals relating to integrated optical density.

5. A method of analysis features in a field according to their spectral characteristics as claimed in claim 3 further comprising the step of computing from a signal comprising constant amplitude pulses produced by comparing the video signal with a reference voltage an electrical signal corresponding in value to the area of that part of the feature to which the constant amplitude pulses relate.

6. A method as claimed in claim 5 further comprising the step of selecting the larger of the two area values computed for a feature.

7. A method as claimed in claim 6 further comprising the step of forming a ratio of the values of the stored signals relating to integrated optical density of each feature and generating a signal indicating the value of the ratio.

8. A method of analysing features in a field according to their spectral characteristics as claimed in claim 5 in which the reference voltage with which the video signal is compared to produce the second mentioned constant amplitude pulses is the same value as that with which the video signal is compared to generate the first mentioned train of constant amplitude pulses.

9. Method of analysis features in a field according to their spectral characteristics as claimed in claim 5 in which the two reference voltages have different values so that the second mentioned constant amplitude pulses relate to a part only of the feature to which the first mentioned constant amplitude pulses relate.

10. Apparatus for analysing features in a field according to their spectral characteristics comprising means for illuminating the field, means for filtering the light from the field according to its wavelength to produce a plurality of separate images thereof, a plurality of scanner means for separately scanning the separate images from the separate filter means to produce a corresponding plurality of separate video signals the amplitudes of which vary in accordance with variations in illumination intensity within the particular image which is presented to that particular scanner means, comparator means for comparing each separate video signal with a reference voltage and generating from the comparison a train of constant amplitude pulses in place of each video signal, a pulse being generated whenever the amplitude of the video signal bears a given relationship to the reference voltage with which it is compared, means for deriving from the video signal an electrical signal whose value corresponds to a parameter of each feature or a portion thereof, means for storing each said computed signal, means having an OR- function for combining the plurality of trains of constant amplitude pulses to produce a pulse train corresponding to that which would be obtained from scanning an image formed by superimposing the said plurality of different images, means for delaying the composite image pulse train for approximately one line scan period, means for comparing the pulses in the delayed composite image signal with the pulses in the current composite image signal, means for generating an anti-coincidence pulse at the end of a delayed composite image signal pulse for which there is no corresponding pulse in the current composite image signal and means for releasing the stored computed signals for each feature in response to the generating of the anti-coincidence pulse therefor.

11. Apparatus for analysing features in a field as claimed in claim 10 further comprising means for forming a ratio of the values of at last two of the stored computed signals released for each feature and circuit means for generating an electrical output signal indicating the value of the ratio.

12. Apparatus for analysing features in a field as claimed in claim 10 further comprising circuit means for forming a signal comprising the logarithm of the analogue amplitude values of the video signal, said computer means serving to accumulate the logarithm signals for each feature to generate a computed signal therefor corresponding to the integrated optical density thereof.

13. Apparatus for analysing features s claimed in claim 12 further comprising comparater means for comparing the video signal with a reference voltage to generate a second train of constant amplitude pulses which constitute the said signal derived from the video signal and computer means for accumulating the constant amplitude pulses relating to each feature for deriving therefrom a signal which will constitute the said stored computed signal for the feature, corresponding to the area thereof.

* * * * *